United States Patent [19]
Debat

[11] 3,984,482
[45] Oct. 5, 1976

[54] 2-(DIHALOBENZYL)-6-NITRO-4-T-BUTYLPHENOL AND PREPARATION THEREOF

[75] Inventor: Jacques Debat, Paris, France

[73] Assignee: Institut de Recherches Chimiques et Biologiques Appliquees I.R.C.E.B.A., Paris, France

[22] Filed: Sept. 25, 1974

[21] Appl. No.: 509,062

Related U.S. Application Data

[60] Division of Ser. No. 267,073, June 28, 1972, Pat. No. 3,855,317, which is a continuation of Ser. No. 755,232, Aug. 26, 1968, abandoned.

[30] Foreign Application Priority Data

Aug. 31, 1967    United Kingdom.............. 39816/67

[52] U.S. Cl. .................... 260/622 R; 260/619 R; 260/623 R; 424/347
[51] Int. Cl.² ............................................. C07C 79/32
[58] Field of Search ......... 260/622 R, 623 R, 619 R

[56]            References Cited
              UNITED STATES PATENTS 3,350,459   10/1967   Pelster ........................... 260/622 R
3,855,317   12/1974   Debat............................. 260/619 R Primary Examiner—James O. Thomas, Jr.
Assistant Examiner—W. B. Lone
Attorney, Agent, or Firm—Bacon & Thomas

[57]            ABSTRACT

The specification describes novel 2-(4'-halobenzyl) phenols of the formula:

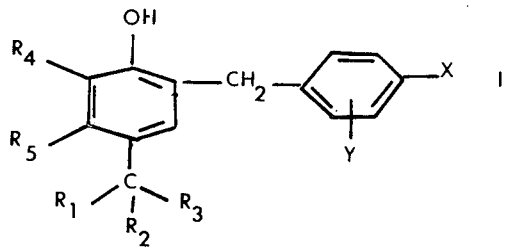

in which $R_1$, $R_2$ and $R_3$, which may be the same or different, are hydrogen or a lower alkyl group, provided that only one of $R_1$, $R_2$ and $R_3$ is hydrogen, or any two or $R_1$, $R_2$ and $R_3$ form, together with the carbon atom to which they are attached, a cycloalkyl ring, particularly cyclohexyl, and the third substituent is hydrogen; $R_4$ is hydrogen, halogen, a nitro group or a benzyl group, the latter, if desired, being substituted in the same manner as the benzyl group shown in the ortho position of the phenolic nucleus; $R_5$ is hydrogen or a hydroxyl group; X is halogen, particularly chlorine or bromine, and Y is hydrogen or halogen, particularly chlorine or bromine, and a process for their preparation. These compounds have useful bacteriostatic activity.

2 Claims, No Drawings

2-(DIHALOBENZYL)-6-NITRO-4-T-BUTYL-PHENOL AND PREPARATION THEREOF

This is a division of application Ser. No. 267,073, filed on June 28, 1972, now U.S. Pat. No. 3,855,317 which is a continuation of application Ser. No. 755,232, filed on Aug. 26, 1968, now abandoned.

This invention is concerned with certain novel 2-(4'-halobenzyl) phenols, with a process for their preparation and with compositions containing them.

We have found that 2-(4'-halobenzyl) phenols of the formula:-

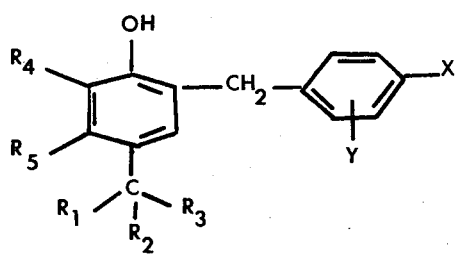

in which $R_1$, $R_2$ and $R_3$, which may be the same or different, are hydrogen or a lower alkyl group, provided that only one of $R_1$, $R_2$ and $R_3$ is hydrogen, or any two of $R_1$, $R_2$ and $R_3$ form, together with the carbon atom to which they are attached, a cycloalkyl ring, particularly cyclohexyl, and the third substituent is hydrogen; $R_4$ is hydrogen, halogen, a nitro group or a benzyl group, the latter, if desired, being substituted in the same manner as the benzyl group shown in the ortho position of the phenolic nucleus; $R_5$ is hydrogen or a hydroxyl group; X is halogen, particularly chlorine or bromine, and Y is hydrogen or halogen, particularly chlorine or bromine, have valuable pharmacological properties. In particular they are effective bacteriostatic agents having high activity accompanied by relatively low toxicity.

Phenol and its derivatives substituted with a methyl group, the cresols, have been used as bacteriostatic agents but they have low bacteriostatic activity. The following inhibiting dilutions were found effective in the conditions, described hereinafter, under which the compounds of Formula I were tested:

| Phenol: 1/1000 | Para-cresol: 1/4000 |
|---|---|

Moreover, these compounds are highly toxic and can only be used externally.

A detailed study of the cresols, their analogues and compounds of similar structure was carried out and it was found that benzyl phenols are more active than cresols with respect to Gram-positive bacteria. It was also found that benzyl cresols in which the methyl group is replaced by a heavier hydrocarbon chain are more active than non-substituted benzyl phenols and a series of benzyl phenol substitution homologues containing straight, branched or cyclic hydrocarbon groups para to the phenol group was accordingly prepared. On testing their activity and toxicity, it was surprisingly found that the benzyl phenols substituted with branched or cyclic hydrocarbon groups were considerably more active than the corresponding straight chain homologues and known analogous compounds. Furhermore, the increase in activity is accompanied by a distinct decrease in toxicity in comparison with the compounds of the other series.

The compounds having the above-described advantages are the compounds of Formula I; these compounds are novel and constitute one aspect of the present invention.

The compounds of Formula I can be prepared by a process which comprises reacting a phenol of the formula:

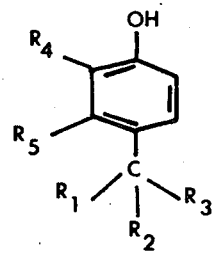

in which $R_1$, $R_2$, $R_3$, $R_4$ and $R_5$ have the above-stated meanings, with a substituted benzyl chloride of the formula:

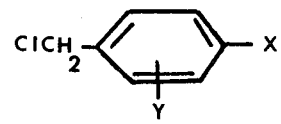

in which X and Y have the above-stated meanings, in the presence of the zinc chloride and preferably in the presence of a solvent, such as chloroforme, at the reflux temperature of the solvent, an excess of the phenol with respect to the substituted benzyl chloride being used when $R_4$ in the desired product is not a substituted benzyl group identical to the substituted benzyl group in the ortho-position of the phenolic ring and an axcess of the substituted benzyl chloride with respect to the phenol being used when $R_4$ in the desired product is a substituted benzyl group identical to the ortho-substituent in the phenolic ring. In order to prepare the nitro compounds (compounds of Formula I in which $R_4$ is $NO_2$), the compounds prepared by this process (using an excess of phenol) are nitrated with nitric acid in glacial acetic acid.

For use in human and veterinary medicine, the compounds of Formula I are generally mixed with an inert physiologically acceptable carrier suitable for the intended mode of administration, most of the compounds can be administered orally for the treatment of infectious diseases; the nitro derivatives (compounds of Formula I in which $R_4$ is $NO_2$) are, however, more suitable for external application.

In order that the invention may be more fully understood, the following Examples are given by way of illustration only. In these Examples, the following general method of preparation was used. Quantities proportional to one mole of phenol and 0.75 mole of mono-halobenzyl chloride or dihalobenzyl chloride are dissolved in 750 ml of anhydrous chloroform. 0.06 mole of crushed fused zinc chloride is then added and the resulting mixture is gently refluxed for between 15 and 24 hours. After cooling, 750 ml of water are added to the reaction mixture, which is then stirred and the organic phase decanted off. The organic phase is washed with water until it reaches a pH of 7 and is then dried on sodium sulphate. The solvent is evaporated and the residue is distilled under reduced pressure.

EXAMPLE 1

2-(4'-chlorobenzyl)-4-sec-butylphenol

The following were used as reagents in the general method described above:
    40 g of p-chlorobenzyl chloride
    45 g of 4-secondary butylphenol
    18 g of fused zinc chloride
    200 ml of dry chloroform The reaction mixture was heated in two periods for a total of 21 hours; liberation of HCl stopped after about 19 hours. 200 ml of cold distilled water were added to the cooled reaction mixture and, after stirring, the organic phase was decanted off. The aqueous phase was extracted twice with 20 ml of chloroform and the chloroformic liquors were combined and washed four times with 25 ml of distilled water. The chloroform solution was dried with 75 g of anhydrous sodium sulphate and, after filtering, a clear solution was obtained. The solvent was evaporated off, first at normal pressure and then under reduced pressure (½ mm Hg), and the residue was distilled. A first fraction distilled over at between 85° and 115°C and consisted of unreacted starting material. A second fraction distilled over at between 160°C and 178°C and consisted of the desired product in a practically pure state. This fraction was recrystallised by dissolving it in 60 ml of boiling petroleum ether and then cooling to −10°C. The resulting product, having an empirical formula $C_{17}H_{19}OCl$ (molecular weight 274.5), melted at 57°C (measured with a Maquenne block).

EXAMPLES 2 to 11

The same general method as described in Example 1 was used in the preparation of the compounds of these Examples, which are identified by their chemical name, empirical formula, molecular weight and one or more of the following constants: melting point (m.p.) measured with a Maquenne block, boiling point (b.p.) at specified pressure in mm Hg, and the refractive index n.

Example 2

2-(4'-chlorobenzyl)-4-isopropylphenol $C_{16}H_{17}OCl = 260.5$ m.p. $= 57°C$

EXAMPLE 3

2-(4'-chlorobenzyl)-4-t-butylphenol $C_{17}H_{19}OCl = 274.5$ m.p. $= 86°C$

EXAMPLE 4

2-(2',4'-dichlorobenzyl)-4-isopropylphenol $C_{16}H_{16}OCl_2 = 295$ b.p. $0.2 = 182°C$ $n^{24} = 1.5888$

EXAMPLE 5

2-(2',4'-dichlorobenzyl)-4-t-butylphenol $n^{22} = 1.5788$

EXAMPLE 6

2-(2',4'-dichlorobenzyl)-4-s-butylphenol $C_{17}H_{18}OCl_2 = 309$ b.p. $0.3 = 170°C$ $n^{24} = 1.5796$

EXAMPLE 7

2-(3',4'-dichlorobenzyl)-4-t-butylphenol $C_{17}H_{18}OCl_2 = 309$ b.p. $0.1 = 174°-177°C$ $n^{22} = 1.5804$

EXAMPLE 8

2-(3',4'-dichlorobenzyl)-4-s-butylphenol $C_{17}H_{18}OCl_2 = 309$ b.p. $0.2 = 160°-162°C$ $n^{21.5} = 1.5779$

EXAMPLE 9

2-(3',4'-dichlorobenzyl)-6-chloro-4-t-butylphenol $C_{17}H_{17}OCl_3 = 343.5$ b.p. $0.3 = 172°-174°C$ $n^{21.5} = 1.5835$

EXAMPLE 10

2-(2',4'-dichlorobenzyl)-6-chloro-4-t-butylphenol $C_{17}H_{17}OCl_3 = 343.5$ b.p. $0.2 = 153°-156°C$ $n^{21.5} = 1.5823$

EXAMPLE 11

2-(3',4'-dichlorobenzyl)-4-isopropylphenol $C_{16}H_{16}OCl_2 = 295$ b.p. $0.4 = 180°-185°C$ $n^{24} = 1.5840$ EXAMPLES 12 and 13

The following method was used to prepare certain compounds of Formula I in which $R^4$ is $NO_2$. 150 ml of glacial acetic acid and 8 g of nitric acid ($d = 1.49$) were placed in a three-necked flask having a capacity of 500 ml. The flask was cooled externally by a cold water bath and was equipped with a reflux condenser and a bromine funnel; it was also provided with a thermometer and an internal magnetic stirrer.

A solution of 17 g of the compound of Example 5 or 7 in 50 ml of glacial acetic acid was added through the bromine funnel over a period of 20 minutes. The temperature of the water bath was then raised over a period of 30 minutes to 70°C and this temperature was maintained for 15 minutes, after which the mixture was left to cool and then poured into 1000 ml of water. The resulting mixture was thoroughly stirred and the oil phase decanted off. Crystallisation in the oil phase was induced by agitation or, if possible, by seeding with a sample of a previous operation.

The resulting crystals were dried, washed with plenty of water and then recrystallised from ethanol; the yield of recrystallised product was 60%.

The following compounds were prepared by the above-described method:

EXAMPLE 12

2-(3',4'-dichlorobenzyl)-6-nitro-4-t-butylphenol
(prepared by nitrating the compound in Example 7)

$C_{17}H_{17}O_3NCl_2 = 354$ m.p. $= 106°C$

EXAMPLE 13

2-(2',4'-dichlorobenzyl)-6-nitro-4-t-butylphenol
(prepared by nitration of the compound in Example 5)

$C_{17}H_{17}O_3NCl_2 = 354$ m.p. 118°C

EXAMPLES 14 to 18

Using the general method described in Example 1, a series of symmetrical dibenzylphenols of the following formula were prepared:

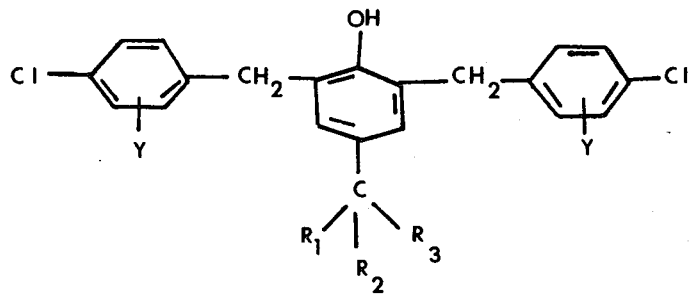

in which $R_1$, $R_2$, $R_3$ and Y have the above-stated meanings.

EXAMPLE 14

2,6-Di(4'-chlorobenzyl)-4-isopropylphenol $C_{23}H_{22}OCl_2 = 385$ m.p. = 93°C

EXAMPLE 15

2,6-Di-(4'-chlorobenzyl)-4-s-butylphenol $C_{24}H_{24}OCl_2 = 399$ m.p. = 93°C

EXAMPLE 16

2,6-Di-(2',4'-dichlorobenzyl)-4-isopropylphenol $C_{23}H_{20}OCl_4 = 454$ b.p. 1 = 250°C

EXAMPLE 17

2,6-Di-(2',4'-dichlorobenzyl)-4-t-butylphenol $C_{24}H_{22}OCl_4 = 468$ b.p. 0.2 = 238°–240°C

EXAMPLE 18

2,6-Di-(3',4'-dichlorobenzyl)-4-t-butylphenol $C_{24}H_{22}OCl_4 = 468$ b.p. 0.2 = 238°–240°C $n^{22} =$ approx. 1.605

EXAMPLES 19 to 21

In these Examples, benzyl phenols of Formula I containing a cyclohexyl radical in the para position of the phenol group were prepared by the method of Example 1.

EXAMPLE 19

2-(4'-chlorobenzyl)-4-cyclohexylphenol $C_{19}H_{21}OCl = 300.5$ m.p. = 105°C

EXAMPLE 20

2-(3',4'-dichlorobenzyl)-4-cyclohexylphenol $C_{19}H_{20}OCl_2 = 335$ m.p. = 84°C

EXAMPLE 21

2-(3',4'-dichlorobenzyl)-4-cyclohexyl-6-chlorophenol $C_{19}H_{19}OCl_3 = 369.5$ b.p. 0.5 = 200°–210°C $n^{24} = 1.5948$

EXAMPLES 22 to 24

The bromobenzyl phenols of these Examples were prepared by the method of Example 1 using the para-bromobenzyl chlorides instead of the chloro-analogue. They have the general formula

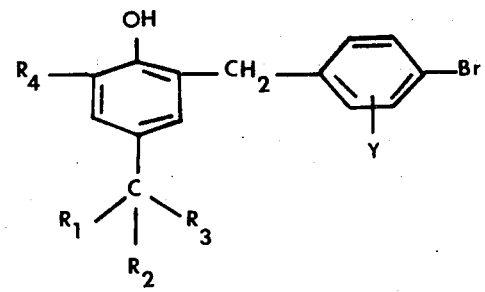

in which $R_1$, $R_2$, $R_3$ $R_4$ and Y have the above-stated meanings.

EXAMPLE 22

2-(4'-bromobenzyl)-4-isopropylphenol $C_{16}H_{17}OBr = 305$ m.p. = 70°C

EXAMPLE 23

2-(4'-bromobenzyl)-4-t-butylphenol $R_1 = H$ m.p. = 88°C

EXAMPLE 24

2-(4'-bromobenzyl)-4-s-butylphenol m.p. 59°C

EXAMPLES 25 to 30

The compounds of these Examples were prepared to compare pharmacologically with the branched-chain compounds of Formula 1.

EXAMPLE 25

2-(4'-chlorobenzyl)-4-methylphenol $C_{14}H_{13}OCl = 232.5$ b.p. 12 = 207°C $n^{24} = 1.5968$

EXAMPLE 26

2-(3',4'-dichlorobenzyl)-4-methylphenol $C_{14}H_{12}OCl_2 = 267$ b.p. 20 = 240°C m.p. = 78°C

EXAMPLE 27

2-(2',4'-dichlorobenzyl)-4-methylphenol $C_{14}H_{12}OCl_2 = 267$ b.p. 13 = 221°C $n^{24} = 1.6100$

EXAMPLE 28

2-(3',4'-dichlorobenzyl)-4-n,hexylphenol $C_{19}H_{22}OCl_2 = 337$ b.p. 0.1 = 221°–224°C $n^{23} = 1.5516$

EXAMPLE 29

2-(4'-chlorobenzyl)-4-n.hexylphenol $C_{19}H_{23}OCl = 302.5$ b.p 0.1 = 215°–218°C $n^{24} = 1.5434$

EXAMPLE 30

2-(2',4'-dichlorobenzyl)-4-n.hexylphenol $C_{19}H_{22}OCl_2 = 337$ b.p. 0.2 = 230°–235°C $n^{23.5} = 1.5491$

EXAMPLES 31 to 34

The compounds of these Examples are benzyl resorcinols substituted with a n-hexyl group para to the OH group of the resorcinol which is adjacent the benzyl group and were also prepared for the purposes of comparison.

EXAMPLE 31

2-(4'-chlorobenzyl)-4-n.hexyl-resorcinol $C_{19}H_{23}O_2Cl = 318.5$ b.p 1.5 = 210°–220°C $n^{25} = 1.559$

EXAMPLE 32

2-(3',4'-dichlorobenzyl)-4-n.hexyl-resorcinol $C_{19}H_{22}O_2Cl_2 = 353$ b.p. 1.5 = 235°–238°C $n^{25} = 1.5782$

EXAMPLE 33

2-(2',4'-dichlorobenzyl)-4-n.hexyl-resorcinol

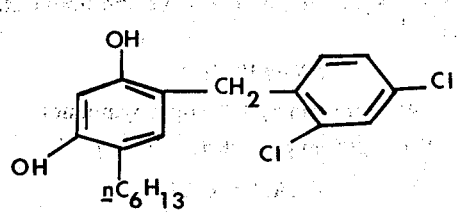

$C_{19}H_{22}O_2Cl_2 = 353$ b.p. 0.4 = 200°–205°C $n^{24} = 1.5763$

EXAMPLE 34

2,6-Di-(4'-chlorobenzyl)-4-n.hexyl-resorcinol $C_{26}H_{28}O_2Cl_2 = 443$ b.p. 0.12 = 220°–235°C $n^{26} = 1.5864$ The known compound of Example 35 was prepared for comparison with the compounds of the invention.

EXAMPLE 35

2-(4'-chlorobenzyl)-4-methoxyphenol $C_{14}H_{13}O_2Cl = 248.5$

The compounds of Formula I were also studied toxicologically and pharmacologically.

The acute toxicity per os was determined in mice by the following method. Different doses of each compound were each tested on 10 mice, both male and female, weighing on average from 18 to 22 g; each dose was administered as a suspension in 10% gum arabic or olive oil and each mouse was given a uniform dose of 0.4 ml per 20 g weight of mouse with the aid of a probang.

The mice were starved for two hours before the experiment and the temperatures and behaviour of the animals were observed before the test and 1½ and 3 hours after ingestion of the compound. After this time they were replaced in their cages and observed for several days.

The number of dead was counted daily and from this was deduced the lethal dose 50 (LD 50), the maxmum tolerated dose (MTD) and the minimum mortal dose MMD). The results are shown in Table I.

TABLE I

| Compound of Example No. | Solvent used | Approximate maximum tolerated dose in g/kg | Approximate LD 50 g/kg |
|---|---|---|---|
| 3 | 10% gum | | 1.9 |
| 4 | Olive oil | 0.5 | 1.7 |
| 7 | Olive oil | 0.5 | 1.5 |
| 2 | Olive oil | 0.5 | 1.7 |
| 1 | 10% gum | 0.5 | 1.0 |
| 8 | Olive oil | 1.0 | 2.4 |
| 10 | Olive oil | 0.5 | 1.5 |
| 9 | Olive oil | 0.5 | above 2.5 |
| 5 | Olive oil | 0.5 | 1.7 |

The results of Table I show that the toxicity (LD 50) of the compounds of the invention is always equal to and often higher than 1.5 g/kg, and sometimes higher than 2.5 g/kg.

The bacteriostatic activities in vitro of the compounds of Formula I were determined by comparing them with known products, particularly of analogous series. The activity was determined with respect to the specific Gram-positive London staphylococcus as a reference strain for all the compounds.

The test was carried out in a culture broth of the following formula:

| Indole-free bacteriological peptone | 40% by weight |
|---|---|
| Sodium chloride | 5% by weight |
| Glucose | 2% by weight |
| pH | 7 – 7.2 |

The method used involved progressive dilution of the principle tested. The dilutions varied by thousandths between concentrations of one thousandth and one tenth of a thousandth, and by 10 thousandths for concentrations between one tenth of a thousandth and 1/100 of a thousandth, and by hundred thousandths for concentrations between 1/100 of a thousandth and one millionth. If the product was found active at a dilution of one millionth, a new range was made from millionth to millionth to beyond one millionth.

Two dilution series were made independently and the results of the two series must be identical. The readings were carried out after 24 hours.

While the activity of formol or cresol is between 1/1,000 and 1/10,000 according to the strain, the compounds of Formula I have an activity of at least 1/30,000 on Gram-positive bacteria. Several of these substances are active at 1/600,000, 1/800,000, 1/1,000,000, and even beyond.

Table II indicates the increase in activity resulting from different substituents. It will be seen in particular that the alkyl substituents containing 3, 4, or more carbon atoms have greater activity than methyl phenols, i.e. derivatives of para-cresol.

TABLE II

| Substituent in para position of phenol | Y = H | | Y at 3' = Cl | | Y at 2' = Cl | |
| --- | --- | --- | --- | --- | --- | --- |
| Methyl (for comparison) | 25* | | 26 | | 27 | |
| | | 1/100,000 | | 1/200,000 | | 1/400,000 |
| Isopropyl | 2 | | 11 | | 4 | |
| | | 1/800,000 | | 1/1,000,000 | | 1/600,000 |
| Sec. butyl | 1 | | 8 | | 6 | |
| | | 1/600,000 | | 1/1,000,000 | | 1/800,000 |
| Ter. butyl | 3 | | 7 | | 5 | |
| | | 1/600,000 | | 1/300,000 | | 1/800,000 |
| Cyclohexyl | 19 | | 20 | | | |
| | | 1/200,000 | | 1/300,000 | | |

*Number of Example showing compound used.

The figure given in the table is that of the maximum dilution at which the growth of London staphylococcus is inhibited.

Activity at a dilution of 1/1,000,000 for the compound of Example 10 and 1/300,000 for the compound of Example 9 was also observed.

The activities of the series of symmetrical dibenzylphenols of Formula (I) are given in Table III.

TABLE III

| Compound of Example No. | Activity with respect to London staphylococcus |
| --- | --- |
| 16 | 1/90,000 |
| 18 | 1/100,000 |
| 14 | 1/40,000 |
| 15 | 1/90,000 |
| 17 | 1/60,000 |

The activities of the bromo derivatives of Formula I are given in Table IV.

TABLE IV

| Compound of Example No. | Activity with respect to Gram-positive London staphylococcus |
| --- | --- |
| 22 | 1/300,000 |
| 23 | 1/200,000 |
| 24 | 1/500,000 |

By comparison with the corresponding chloro derivatives of Examples 1, 2 and 3, which have activities of 1/600,000, 1/600,000 and 1/800,000, respectively, it can be seen that the replacement of chlorine by bromine causes a lowering of activity with respect to Gram-positive bacteria.

I claim:
1. The compound 2-(3',4'-dichlorobenzyl)-6-nitro-4-t-butylphenol.
2. The compound 2-(2',4'-dichlorobenzyl)-6-nitro-4-t-butylphenol.

* * * * *